United States Patent
Wu et al.

(10) Patent No.: US 9,808,202 B2
(45) Date of Patent: Nov. 7, 2017

(54) MATTRESS FOR MEASURING PHYSIOLOGICAL PARAMETERS OF HEART

(71) Applicant: Shenzhen Novocare Medical Devices Co., Ltd, Shenzhen (CN)

(72) Inventors: Zhengyu Wu, Shenzhen (CN); Yuanting Zhang, Shenzhen (CN); Xuefang Yang, Shenzhen (CN)

(73) Assignee: Shenzhen Novocare Medical Devices Co, INC, Shenzhen (CN)

( * ) Notice: Subject to any disclaimer, the term of this patent is extended or adjusted under 35 U.S.C. 154(b) by 0 days.

(21) Appl. No.: 14/932,861

(22) Filed: Nov. 4, 2015

(65) Prior Publication Data

US 2016/0151020 A1    Jun. 2, 2016

(30) Foreign Application Priority Data

Nov. 28, 2014   (CN) .......................... 2014 1 0709449
Nov. 28, 2014   (CN) .......................... 2014 1 0709469
Nov. 28, 2014   (CN) .......................... 2014 1 0709756

(51) Int. Cl.
   *A61B 5/0408*   (2006.01)
   *A61B 5/00*     (2006.01)

(52) U.S. Cl.
   CPC .......... *A61B 5/6892* (2013.01); *A61B 5/0408* (2013.01); *A61B 5/4806* (2013.01); *A61B 2562/182* (2013.01)

(58) Field of Classification Search
   CPC ... A61B 5/0402; A61B 50/24; A61B 1/14552; A61B 5/6887; A61B 5/1102; A61B 5/04012; A61B 5/053; A61B 2018/00839; A61B 5/0006; A61B 5/0245; A61B 5/0531; A61B 5/6891; A61B 5/6892;
   (Continued)

(56) References Cited

U.S. PATENT DOCUMENTS 2,409,033 A * 10/1946 Garceau ............... A61B 5/0476 330/120
3,720,209 A *  3/1973 Bolduc ............... A61B 5/0416 128/908

(Continued)

FOREIGN PATENT DOCUMENTS

CN    104398358 A    3/2015
CN    104411150 A    3/2015

*Primary Examiner* — Kennedy Schaetzle
(74) *Attorney, Agent, or Firm* — Treasure IP Group, LLC

(57) ABSTRACT

The present invention provides a mattress for measuring physiological parameters of a heart, comprising a mattress body, a first electrode, a second electrode and an electromagnetic shield, wherein the first electrode and the second electrode are located on the upper surface of the mattress body and the first electrode and the second electrode have a space therebetween; at least a portion of the electromagnetic shield is located on the lower surface of the mattress body and is insulated from the first electrode and the second electrode. In the above mattress provided by the present invention, the first electrode and the second electrode are shielded from ambient electromagnetic radiation effectively. The electromagnetic shield, by blocking the electromagnetic wave propagation path, prevents the electrodes from being polluted by electromagnetic radiation, achieving more accurate measurement.

16 Claims, 15 Drawing Sheets

(58) Field of Classification Search
CPC .......... A61B 2505/07; A61B 2562/164; A61B 2562/0214; A61B 5/04
USPC .......................................................... 600/509
See application file for complete search history.

(56) References Cited

U.S. PATENT DOCUMENTS

| | | | | |
|---|---|---|---|---|
| 3,760,794 | A * | 9/1973 | Basham | A61B 5/6892 340/573.1 |
| 4,033,332 | A * | 7/1977 | Hardway, Jr. | A61B 5/1118 324/611 |
| 4,365,636 | A * | 12/1982 | Barker | A61B 5/113 600/529 |
| 5,458,124 | A * | 10/1995 | Stanko | A61B 5/0006 128/903 |
| 6,840,907 | B1 * | 1/2005 | Brydon | A61B 5/113 600/534 |
| 7,684,854 | B2 * | 3/2010 | Park | A61B 5/0428 600/382 |
| 8,483,811 | B2 * | 7/2013 | Ueda | A61B 5/0205 600/508 |
| 8,583,206 | B2 * | 11/2013 | Brauers | A61B 5/04085 600/372 |
| 8,798,708 | B2 * | 8/2014 | Tremblay | A41D 13/1281 600/388 |
| 2006/0041196 | A1 * | 2/2006 | Matthews | A61B 5/04085 600/393 |
| 2007/0255152 | A1 * | 11/2007 | Park | A61B 5/0428 600/513 |
| 2008/0208063 | A1 * | 8/2008 | Brauers | A61B 5/04085 600/481 |
| 2010/0262026 | A1 * | 10/2010 | Meftah | A61B 5/04011 600/509 |
| 2011/0034811 | A1 * | 2/2011 | Naujokat | A61B 5/0245 600/484 |
| 2014/0323838 | A1 * | 10/2014 | Nishii | A61B 5/6891 600/382 |
| 2016/0121074 | A1 * | 5/2016 | Ashby | A61M 21/02 600/28 |
| 2016/0287128 | A1 * | 10/2016 | Jain | A61B 5/6844 |

* cited by examiner

MATTRESS FOR MEASURING PHYSIOLOGICAL PARAMETERS OF HEART

CROSS REFERENCE TO RELATED APPLICATION

This application claims priority to Chinese Application No. 201410709449.5, filed on Nov. 28, 2014; Chinese Application No. 201410709469.2, filed on Nov. 28, 2014; and Chinese Application No. 201410709756.3, filed on Nov. 28, 2014. The Chinese Applications are incorporated herein by reference in their entireties.

FIELD OF INVENTION

The present invention relates generally to the field of medical supplies, and more particularly to a mattress for measuring physiological parameters of a heart.

BACKGROUND

As living standards increase every day, people have been paying more attention to their own health conditions. This is particularly true with those people facing physical health problems, who may expect to monitor some physiological parameters of their body in real time, such as patients with cardiovascular diseases who may desire real-time monitoring of physiological parameters of their hearts by virtue of electrodes.

The development of technology strongly supports the abovementioned demands of people. So far, there have been all kinds of electrodes for conveniently measuring physiological parameters human hearts.

Nevertheless, on the one hand, electromagnetic pollution in the environment has caused disturbances to measurement of physiological parameters of the heart. Also, brain cell masses and muscle cell masses also have spontaneous, rhythmic electrical activities that interfere with measurement by the abovementioned electrodes, making it hard for people to obtain accurate measurement results.

SUMMARY OF THE INVENTION

According to one aspect of the present invention, a mattress for measuring physiological parameters of a heart is provided, comprising a mattress body, a first electrode, a second electrode and an electromagnetic shield, wherein the first electrode and the second electrode are located on the upper surface of the mattress body and the first electrode and the second electrode have a space therebetween; at least a portion of the electromagnetic shield is located on the lower surface of the mattress body and is insulated from the first electrode and the second electrode.

In the abovementioned mattress provided by the present invention, the first electrode and the second electrode are effectively shielded from ambient electromagnetic radiation. The electromagnetic shield, by blocking the electromagnetic wave propagation path, prevents the electrodes from being polluted by electromagnetic radiation, enabling more accurate measurement.

A series of simplified concepts are introduced in the Summary of the Invention, which will be further explained in the Detailed Description. The Summary of the Invention is not intended for defining critical features and essential technical features of the technical solution for which protection is sought, and still less intended for determining the protection scope of the technical solution for which protection is sought.

Advantages and features of the present invention will be described in detail below in connection with the accompanying drawings.

BRIEF DESCRIPTION OF THE DRAWINGS

The accompanying drawings described below are hereby included as part of the present invention to facilitate understanding of the invention. The drawings illustrate embodiments of the present invention and the descriptions thereof, for the sake of expounding the principles of the present invention. In the accompanying drawings.

DETAILED DESCRIPTION

In the following discussion, details are presented so as to provide a more thorough understanding of the present invention. However, as would be known by persons skilled in the art, the following descriptions only concern preferred embodiments of the present invention, and the present invention may be implemented without one or more of these details. Certain technical features well known in the art are not depicted herein so as to avoid confusion with the present invention.

According to one aspect of the present invention, a mattress is provided. The mattress may be placed on a bed in a hospital or at home. A user wearing pajamas may lie on the mattress directly or with a bed sheet spread thereon. The mattress can measure physiological parameters of the heart of the user lying on the mattress.

Figure 1:
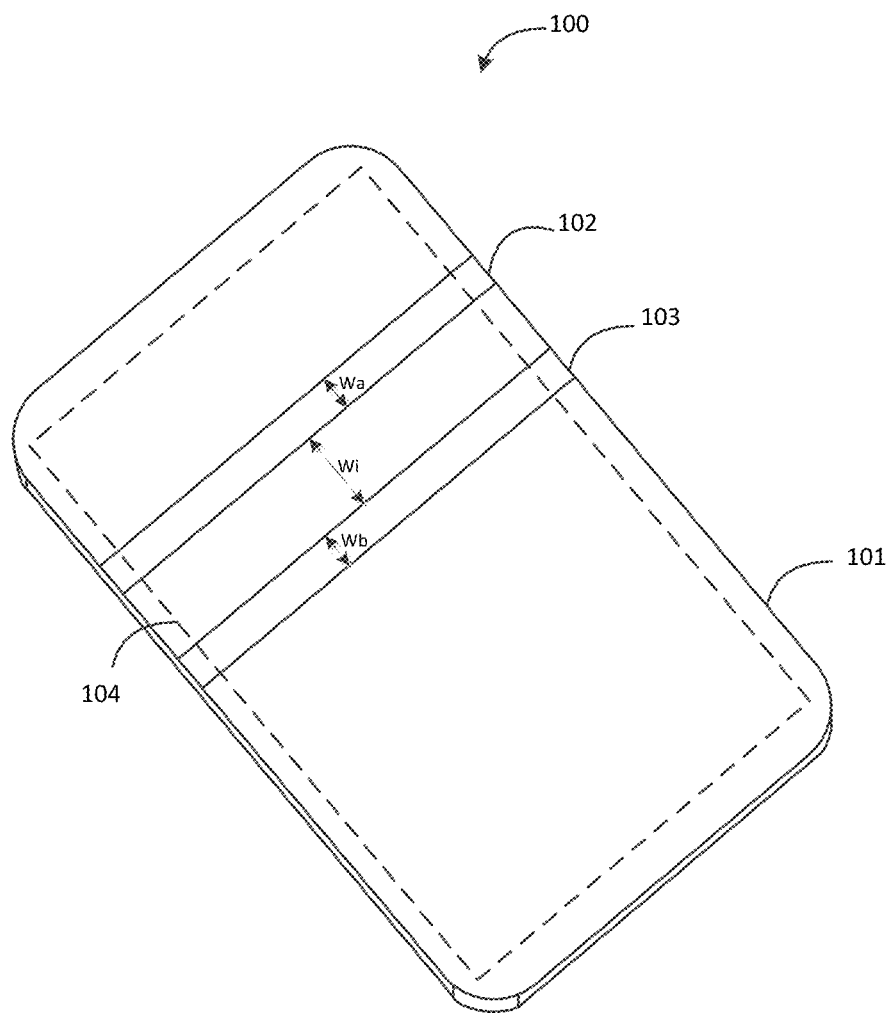
FIG. 1 is a schematic diagram of a mattress for measuring physiological parameters of a heart according to one embodiment of the present invention.

FIG. 1 illustrates a mattress 100 for measuring physiological parameters of the heart according to one embodiment of the present invention. As shown in FIG. 1, the mattress 100 comprises a mattress body 101, a first electrode 102, a second electrode 103 and an electromagnetic shield 104. Wherein, the first electrode 102 and the second electrode 103 are located on an upper surface of the mattress body 101 and the first electrode 102 and the second electrode 103 has a space therebetween. At least a portion of the electromagnetic shield 104 is located on a lower surface of the mattress body 101 and is insulated from the first electrode 102 and the second electrode 103.

Physiological parameters of a heart are a comprehensive reflection of electric activities of numerous myocardial cells of the heart, and may manifest as a potential difference signal on the body surface. The potential difference signal may be called as an electrocardiosignal. In the embodiment of the present invention, the first electrode 102 and the second electrode 103 are used to collect electrocardiosignals of the human body. The first electrode 102 and the second electrode 103 may constitute a capacitance, the two capacitively coupling to the electrocardio potential on the body surface. When the mattress 100 is in use, the user usually lies in such a position that the heart is located between the first electrode 102 and the second electrode 103, so that the first electrode 102 and the second electrode 103 measure the potential difference between the upper and lower positions of the heart.

The interactions between the time-varying electric fields and the time-varying magnetic fields generate electromagnetic waves. The phenomenon of electromagnetic waves being emitted into or converged in the air is defined as electromagnetic radiation. Excessive electromagnetic radiation causes electromagnetic pollution, which is interference among various natural or artificial electromagnetic waves. Since the electrocardiosignal is characterized by a weak signal, the electrocardiosignal collection by the first electrode 102 and the second electrode 103 is susceptible to electromagnetic interference. In the embodiment of the present invention, at least a portion of the electromagnetic shield 104 is located on the lower surface of the mattress body 101, and is insulated from the first electrode 102 and the second electrode 103. As shown in FIG. 1, the electromagnetic shield 104 is insulated from the first electrode 102 and the second electrode 103 by the mattress body 101. The electromagnetic shield 104 has the functions of absorbing, reflecting and offsetting energy of interfering electromagnetic waves in the environment, and thus, the electromagnetic shield 104 diminishes the electromagnetic interferences suffered by the first electrode 102 and the second electrode 103. Specifically, when electromagnetic waves arrive at the surface of the electromagnetic shield 104, due to discontinuous impedance on the interface between air and the electromagnetic shield 104, incident electromagnetic waves are reflected. The energy that is not reflected by the surface and enters into the electromagnetic shield 104 is attenuated by the electromagnetic shield 104 during its propagation toward the first electrode 102 and the second electrode 103 in the electromagnetic shield 104. Remaining energy that is not attenuated in the electromagnetic shield 104, when leaving the electromagnetic shield 104, reencounters the discontinuous-impedance interface between the electromagnetic shield 104 and air, and is reflected again and returns into the electromagnetic shield 104. Such reflection may occur multiple times on the interface between the electromagnetic shield 104 and air. In a word, to the first electrode 102 and the second electrode 103, the electromagnetic shield 104 performs the electromagnetic shielding function effectively.

The abovementioned mattress 100 provided in the present invention can effectively shield the first electrode 102 and the second electrode 103 from ambient electromagnetic radiation. With the electromagnetic shield 104 blocking the electromagnetic wave propagation path, the first electrode 102 and the second electrode 103 are screened from pollution and interference by electromagnetic radiation, thus enabling more accurate measurement to physiological parameters of the heart.

Figure 2:
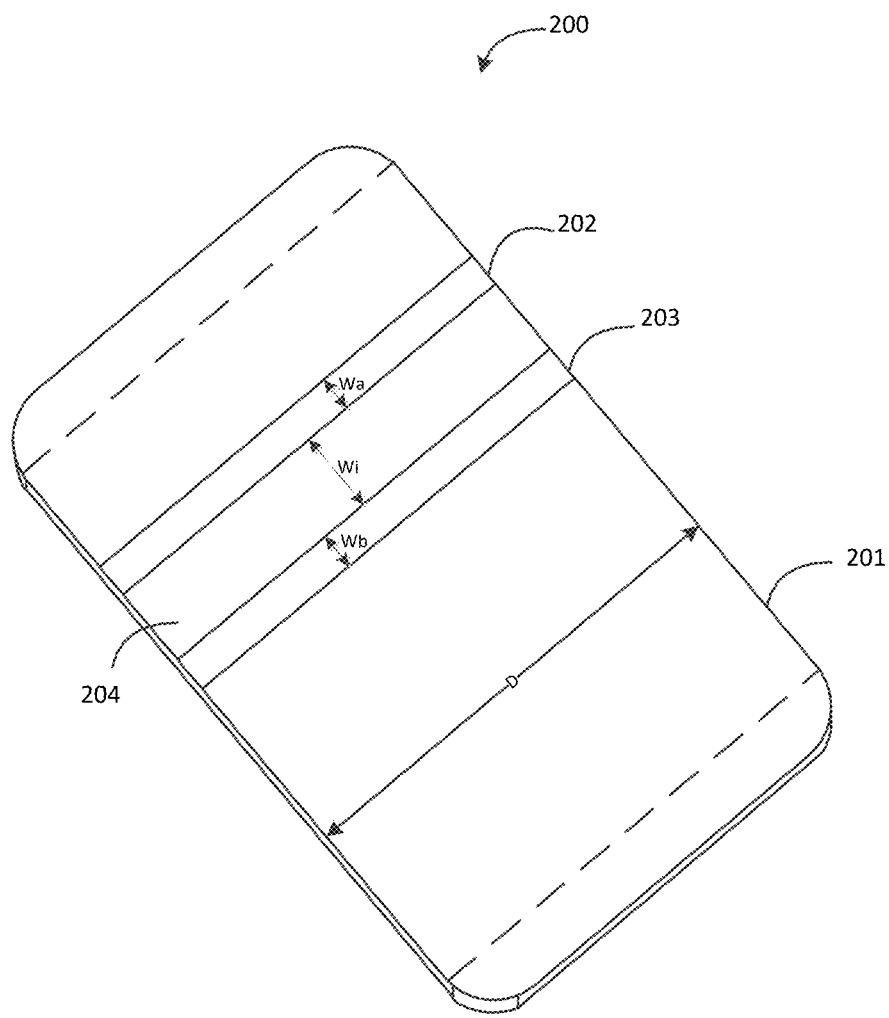
FIG. 2 is a schematic diagram of a mattress for measuring physiological parameters of a heart according to another embodiment of the present invention.

FIG. 2 illustrates a mattress 200 according to another embodiment of the present invention. As shown in FIG. 2, the mattress 200 comprises a mattress body 201, a first electrode 202, a second electrode 203 and an electromagnetic shield 204. The function of and positional relationship among the mattress body 201, the first electrode 202, the second electrode 203 and the electromagnetic shield 204 are similar to those of the mattress body 101, the first electrode 102, the second electrode 103 and the electromagnetic shield 104, and thus will not be described herein. However, as shown in FIG. 2, the electromagnetic shield 204 has a width equal to that of the mattress body 201. As is seen in FIG. 2, both have a width D. Being equal in width to the mattress body 201, the electromagnetic shield 204 can block more electromagnetic waves away from the first electrode 202 and the second electrode 203.

Furthermore, the portion of the electromagnetic shield located on the lower surface of the mattress body can cover the entire lower surface of the mattress body, so as to block out more electromagnetic waves coming from under the mattress body. In this way, a better measurement environment is provided for the first electrode and the second electrode, so as for them to provide more accurate measurement results for the user.

According to one embodiment, the electromagnetic shield may comprise a first portion and a second portion, wherein the first portion is located on the upper surface of the mattress body, and the second portion is located on the lower surface of the mattress body, with the two portions being electrically connected. The electrical connection is, for example, by means of a wire. The first portion of the electromagnetic shield assists the second portion of the electromagnetic shield in electromagnetic shielding, effectively shielding out electromagnetic interference coming from the surroundings of the mattress. In particular, spontaneous and rhythmic electric activities of brain cell masses and muscle cell masses generate electroencephalographic (EEG) signals and electromyographic signals respectively, which will also cause electromagnetic pollution. The first portion located on the upper surface of the mattress body can effectively shield noise interference by electroencephalographic (EEG) signals and/or electromyographic signals.

Figure 3A:
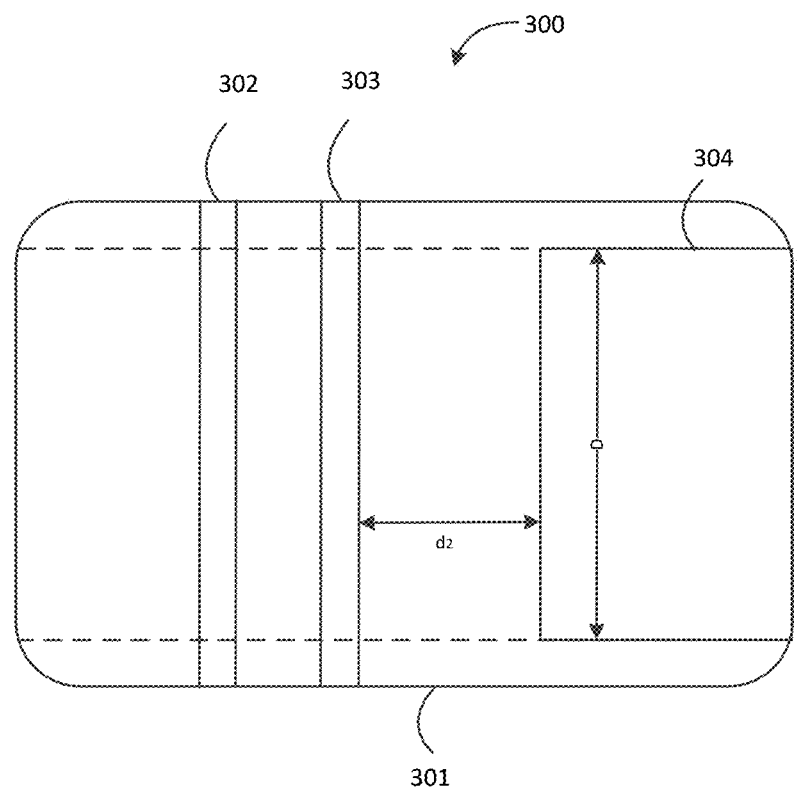
FIG. 3a and FIG. 3b illustrate a top view and a sectional view, respectively, for a mattress for measuring physiological parameters of a heart according to yet another embodiment of the present invention.
Figure 3B:
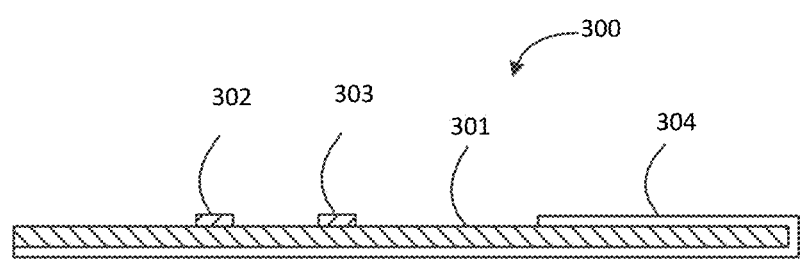

FIGS. 3a and 3b illustrate a top view and a sectional view, respectively, of a mattress 300 according to yet another embodiment of the present invention. As shown in FIGS. 3a and 3b, the mattress 300 comprises a mattress body 301, a first electrode 302, a second electrode 303 and an electromagnetic shield 304. The mattress 300 is similar to the mattress 100, and is only distinguished in that, as shown in FIGS. 3a and 3b, the electromagnetic shield 304 can extend from the lower surface of the mattress body 301 along the tail of the mattress body 301 to the upper surface of the mattress body 301 in the width D of the electromagnetic shield 304. When the mattress is in use, the portion corresponding to the bed tail is called the tail of the mattress body.

In this embodiment, the electromagnetic shield 304 extends onto the upper surface in its own width D, and it is an integrated piece with no apparent gap therein. This approach avoids some gaps in the spatial structure between the first portion and the second portion of the abovementioned electromagnetic shield. Skin current formed by charge induced by the electromagnetic wave would flow along the outer surface of the electromagnetic shield. When the skin current encounters a gap, the current runs through the gap to enter the space between the first portion and the second portion, and thereby, an electric field is formed in the space. As a consequence, the shielding effect of the electromagnetic shield is diminished. The electromagnetic shield 304 solves this problem and ensures the electromagnetic shielding effect. What's more, the design that the electromagnetic shield 304 extends onto the upper surface in its own width D simplifies the mattress manufacturing process.

If the electromagnetic shield 304 is too close to the second electrode 303, it is inclined to cause interference with the measurement of the first and second electrodes. When the mattress is in use, the second electrode 303 is usually located at the lower end of the heart of the human body. Moreover, electromyographic signals are mainly generated by the buttocks and thighs of the human body. On the upper surface of the mattress body 301, preferably, the distance $d_2$ between the electromagnetic shield 304 and the second electrode 303 is from 20 cm to 40 cm. In the above design, noise interference caused by electromyographic signals and other electromagnetic interferences are more effectively shielded, while interference with the measurements of the first and second electrodes is avoided.

It would be appreciated by those skilled in the art that the electromagnetic shield may also extend from the lower surface of the mattress body along the head of the mattress body onto the upper surface of the mattress body in the width D of the electromagnetic shield. When the mattress is in use, the portion corresponding to the head of the bed is defined as the head of the mattress body. Similarly, when the mattress is in use, the first electrode is usually located at the upper end of the heart of the human body. Moreover, electroencephalographic (EEG) signals are mainly generated by the head of the human body. On the upper surface of the mattress body, preferably, the distance $d_1$ between the electromagnetic shield and the first electrode is from 12 cm to 25 cm. This more effectively shields noise interference caused by electroencephalographic (EEG) signals and other electromagnetic interferences, while avoiding interference with the measurements of the first and second electrodes.

Figure 4A:
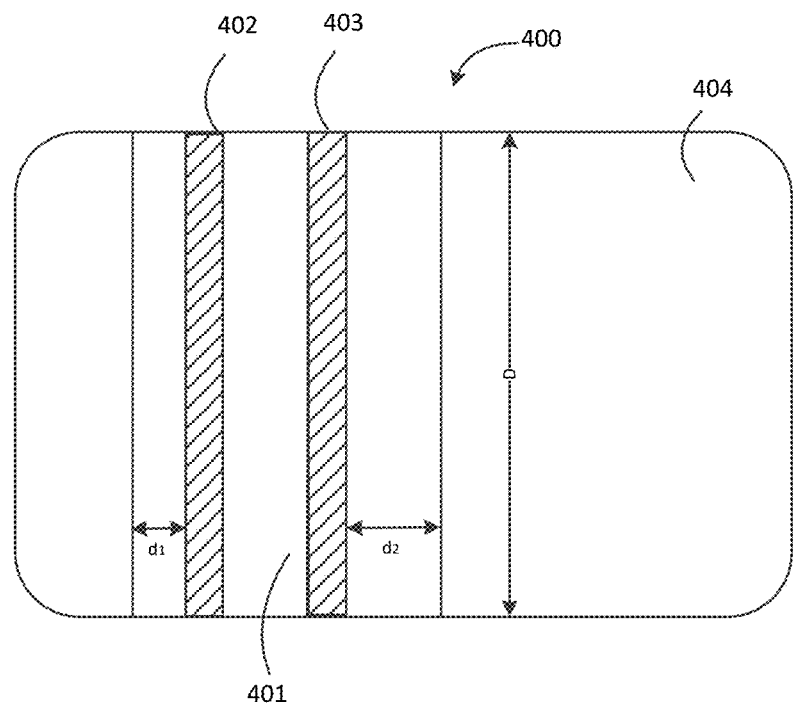
FIG. 4a and FIG. 4b illustrate a top view and a sectional view, respectively, for a mattress for measuring physiological parameters of a heart according to still another embodiment of the present invention.
Figure 4B:
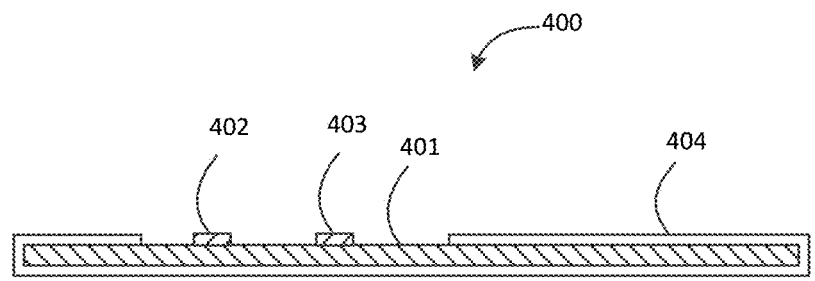

According to one embodiment of the present invention, the electromagnetic shield may extend from the lower surface of the mattress body along the head and the tail of the mattress body, respectively, onto the upper surface of the mattress body in the width of the electromagnetic shield. Similar to the above discussions, by extending from the head and the tail to the upper surface of the mattress body in the width of the electromagnetic shield, the shielding effect of the electromagnetic shield against electromagnetic interferences of electroencephalographic (EEG) and electromyographic signals and other electromagnetic interferences in the environment is improved. FIGS. 4a and 4b illustrate a top view and a sectional view respectively of a mattress 400 for measuring physiological parameters of a heart according to yet another embodiment of the present invention. The mattress 400 is similar to the mattress 200, except that in the mattress 400, the electromagnetic shield 404 extends from the lower surface of the mattress body 401 along the head and the tail of the mattress body 401 respectively to the upper surface of the mattress body 401 in the width D of the electromagnetic shield, so as to effectively shield the noise interference caused by electroencephalogram and myoelectricity and other environmental interferences.

Figure 5A:
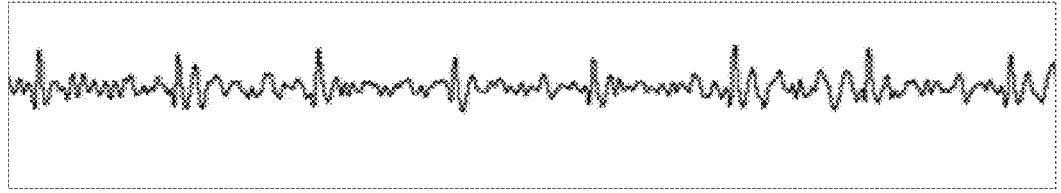
FIG. 5a and FIG. 5b respectively illustrate an oscillogram of physiological parameters of user A collected by use of different mattresses, and FIG. 5c and FIG. 5d respectively, illustrate an oscillogram of physiological parameters of user B collected by use of different mattresses.
Figure 5B:
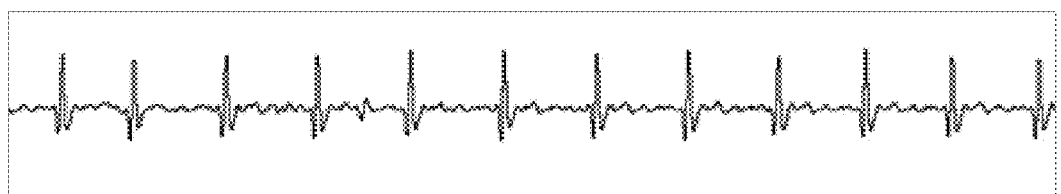
Figure 5C:
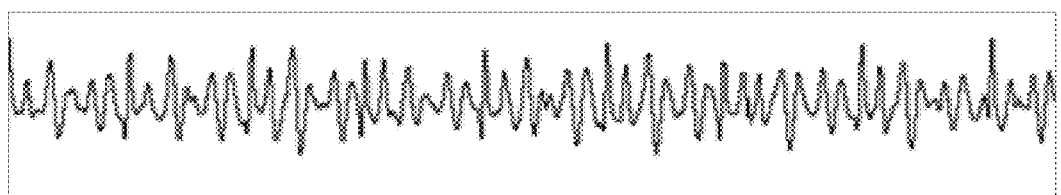
Figure 5D:
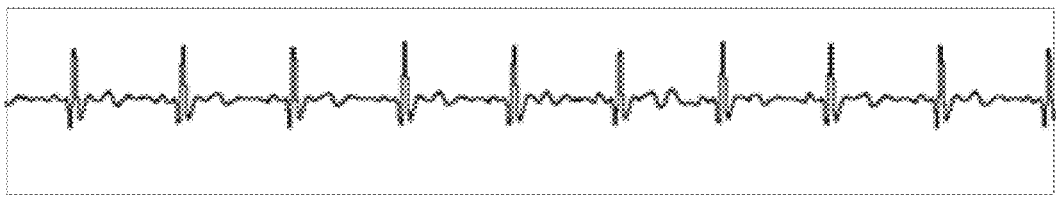

FIGS. 5a and 5b respectively illustrate an oscillogram of physiological parameters of user A collected by use of different mattresses, and FIG. 5c and FIG. 5d, respectively, illustrate an oscillogram of physiological parameters of user B collected by use of different mattresses. In FIGS. 5a-5d, the horizontal axis of the oscillogram denotes time, and the vertical axis of the oscillogram denotes voltage representing the value of physiological parameters of the heart, wherein, the oscillograms in FIGS. 5a and 5c are collected by using a mattress without an electromagnetic shield. The oscillograms in FIGS. 5b and 5d are collected by using the mattress 400, wherein in the mattress 400, the electromagnetic shield 404 extends on the upper surface of the mattress body 401 to a position at a distance $d_1$ of 20 cm from the first electrode 402 and at a distance $d_2$ of 30 cm from the second electrode 403. As shown in the figures, FIGS. 5a and 5b are in sharp contrast, wherein the oscillogram in FIG. 5a is unable to show distinctly a peak value and a period of waveform, for the very reason that the electrodes in the mattress are subject to electromagnetic interference. In contrast, the oscillogram in FIG. 5b shows distinctly a peak value and a period of waveform, which may be applied to effectively analyze physiological parameters of the user A's heart. The above conclusion also can be drawn from the oscillograms in FIGS. 5c and 5d, which will not be described herein.

An appropriate distance between the electromagnetic shield and the electrode ensures accurate measurement of the electrodes free of interference. As is shown by experimental data, on the upper surface of the mattress body 401, when the distance $d_1$ between the electromagnetic shield 404 and the first electrode 402 and the distance $d_2$ between the electromagnetic shield 404 and the second electrode 403 meet the following condition: $d_2=a*d_1$, relatively effective shielding against noise interferences generated by both electromyographic signals and EEG signals can be achieved, wherein a $\in[1, 2]$, that is, a is any real number in the closed interval. For example, $d_1=20$ cm, $d_2=30$ cm.

According to one embodiment of the present invention, the electromagnetic shield has an end edge on the upper surface of the mattress body that is parallel to the head of the mattress, as shown in FIGS. 1-4b. The head of the mattress refers to the portion corresponding to the head of the bed when the mattress is in use. The end edge of the electromagnetic shield being parallel to the head of the mattress guarantees that the electrodes can still receive effective shielding from the electromagnetic shield when the user turns over on the mattress.

Figure 6:
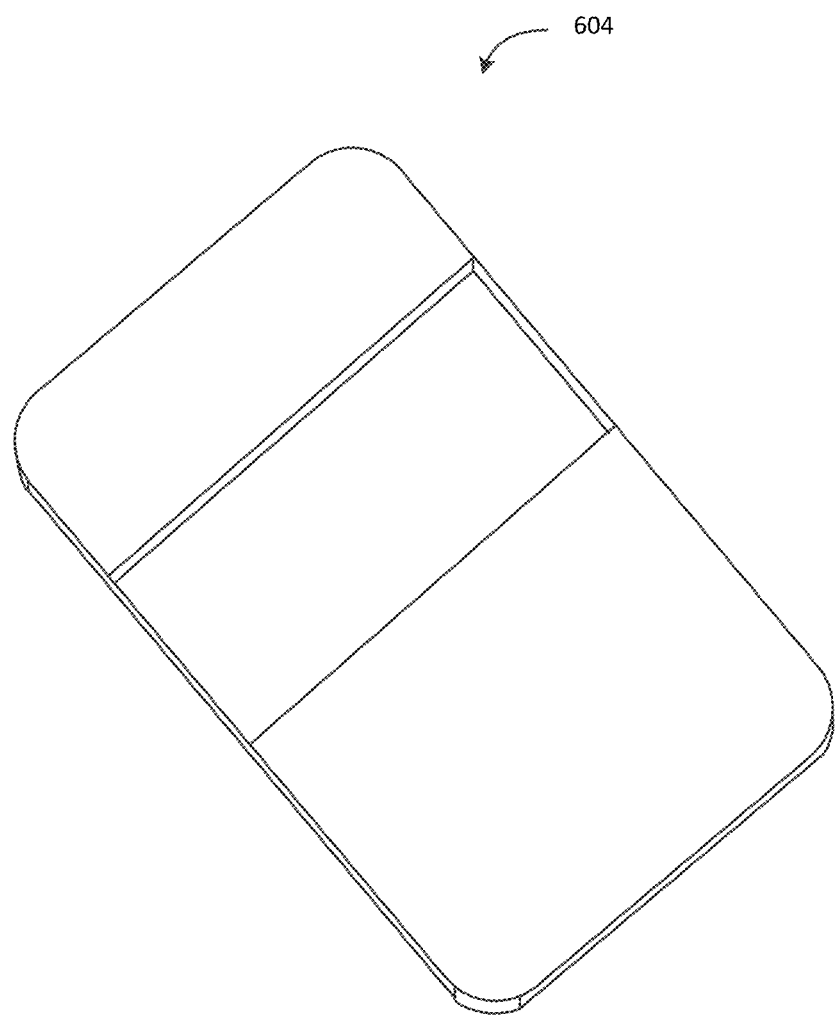
FIG. 6 is a schematic diagram of an electromagnetic shield according to one embodiment of the present invention.

According to one embodiment of the present invention, the electromagnetic shield has a width equal to that of the mattress body, and the portion of the electromagnetic shield located on the upper surface of the mattress body is completely connected with the portion of the electromagnetic shield located on the lower surface of the mattress body on both side edges. The side edges of the electromagnetic shield refer to the edges corresponding to the side portion of the bed when the mattress in use. For example, the portion of the electromagnetic shield located on the upper surface of the mattress body and the portion thereof located on the lower surface of the mattress body may be stitched up together. For another instance, the electromagnetic shield is made by once forming method. FIG. 6 illustrates an electromagnetic shield 604 according to one embodiment of the present invention. As shown in FIG. 6, the electromagnetic shield 604 has two cavities corresponding to the head and the tail of the mattress body, respectively. The head and the tail of the mattress body are put into the two cavities formed by the electromagnetic shield, respectively, and then, the electrodes are placed on the upper surface of the mattress body. This ensures that there is no gap between the portion of the electromagnetic shield located on the upper surface of the mattress body and the portion thereof located on the lower surface of the mattress body, preventing the electromagnetic wave induced skin current from flowing into the space where the electrodes are located, thus enhancing the shielding effect of the electromagnetic shield and further ensuring the measurement accuracy of the electrodes.

According to one embodiment of the present invention, the electromagnetic shield may extend from the lower surface of the mattress body along the side of the mattress body to the upper surface of the mattress body in the length of the electromagnetic shield. The side of the mattress body refers to a side that is corresponding to the side portion of the bed when the mattress in use. As discussed above in detail, this approach can achieve better electromagnetic shielding.

According to one embodiment of the present invention, the electromagnetic shield can be electrically connected to the ground wire. This connection is, for example, by means of a conductive button. In this way, the charge on the surface of the electromagnetic shield is conducted to the ground via the ground wire, so as to further enhance the electromagnetic shielding effect.

According to one embodiment of the present invention, the electromagnetic shield comprises a first layer of electric conductor and a second layer of electrical conductor that are insulated from each other. The first layer of electrical conductor has a lower electrical resistivity as well as a lower magnetoconductivity than the second layer of electric conductor. Optionally, the material of the first layer of electrical conductor includes silver, copper or aluminum, and the material of the second layer of electric conductor includes steel or iron. When the interfering electromagnetic waves are of a relatively high frequency, the vortex generated in the first layer of electrical conductor having a lower electrical resistivity is utilized efficiently to perform the function of offsetting electromagnetic waves in the environment, so as to achieve the shielding effect. When the interfering electromagnetic waves are of a relatively low frequency, the second layer of electrical conductor having high magnetoconductivity is utilized to restrict the magnetic field lines within the electromagnetic shield, and prevents them from spreading to the electrodes. In a word, the double-layer electromagnetic shield not only effectively shields low-frequency electromagnetic waves, but also high-frequency electromagnetic waves.

According to one embodiment of the present invention, the first electrode and the second electrode are rectangular and parallel to each other, and the first electrode and the second electrode are parallel to the head of the mattress. When the mattress is in use, the portion corresponding to the head of the bed is called the head of the mattress. As mentioned above, signals of physiological parameters of the human heart are very weak, and are usually interfered by various noises, such as human body movements. Still referring to FIG. 1, the first electrode 102 and the second electrode 103 may be rectangular and be one integrated piece. This allows the human body to turn over on the mattress 100, while still maintaining relatively large contact areas with the first electrode 102 and the second electrode 103. The first electrode 102 and the second electrode 103 are parallel to each other, and the first electrode 102 and the second electrode 103 are parallel to the head of the mattress 100. This enables the space between the first electrode 102 and the second electrode 103 to be constant. In this way, turning movements of the human body on the mattress 100 do not affect measurement results for the physiological parameters of the heart, effectively ensuring the accuracy of the measurement results.

Figure 7:
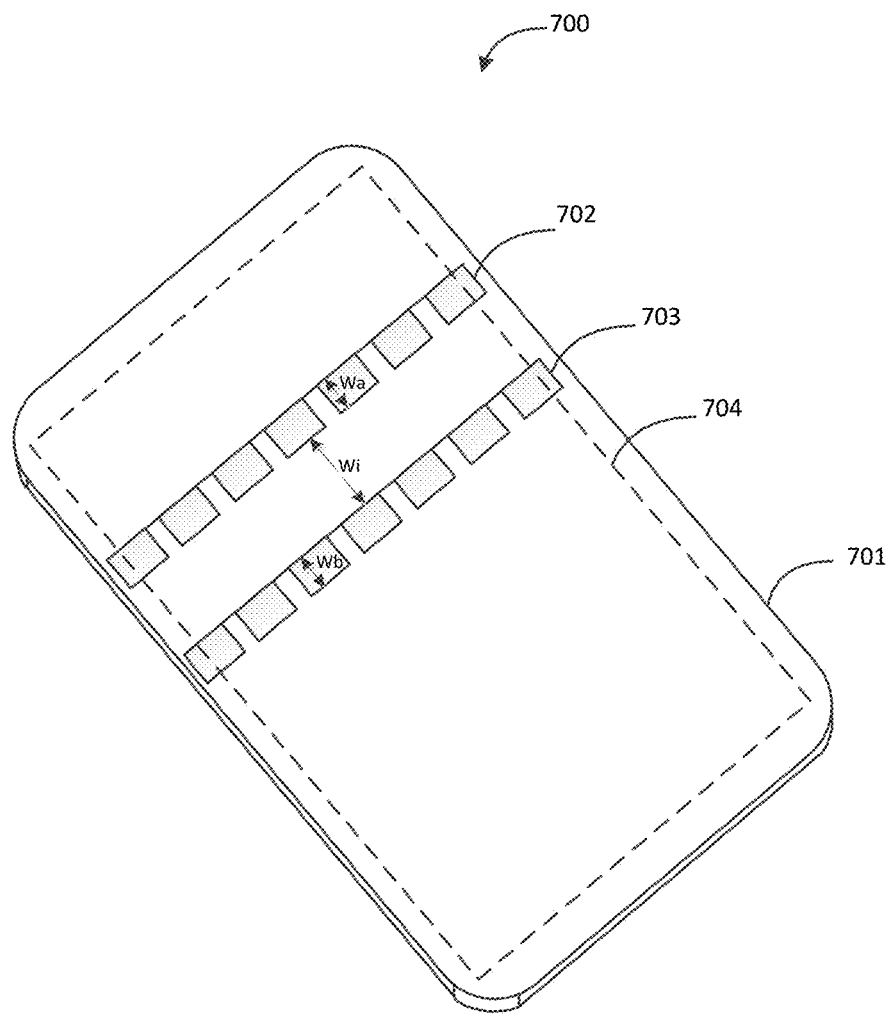
FIG. 7 is a schematic diagram of a mattress for measuring physiological parameters of a heart according to another embodiment of the present invention.

FIG. 7 illustrates a mattress 700 for measuring physiological parameters of a heart according to another embodiment of the present invention. The mattress 700 comprises a mattress body 701, a first electrode 702, a second electrode 703 and an electromagnetic shield 704. The mattress 700 is similar to the mattress 100, with the only distinction that in the mattress 700, the first electrode 702 and the second electrode 703 in mattress 700 are arrays of multiple electrically connected sub-electrodes. Due to reduction of electrode area, this arrangement of the mattress 700 requires fewer electrode materials.

Figure 8A:
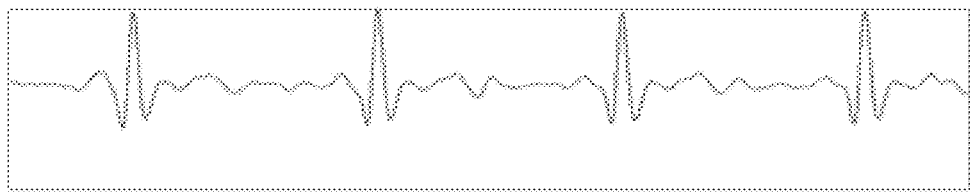
FIGS. 8a-8f respectively illustrate an oscillogram of physiological parameters of the heart of user A collected by use of different mattresses.
Figure 8B:
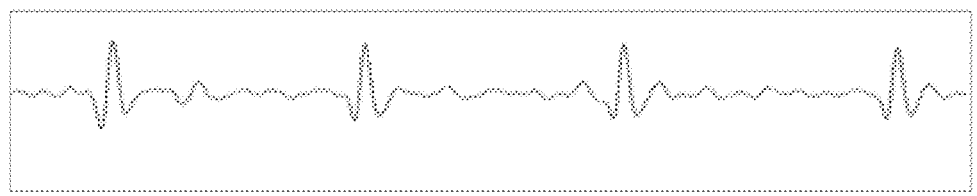
Figure 8C:
Figure 8D:
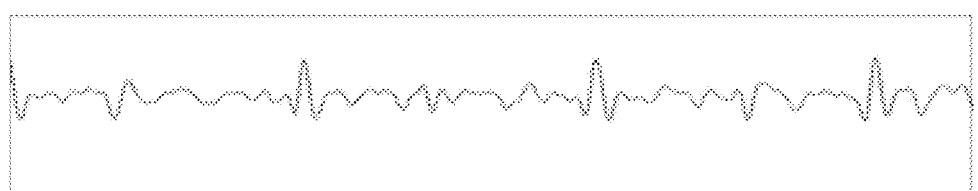
Figure 8E:
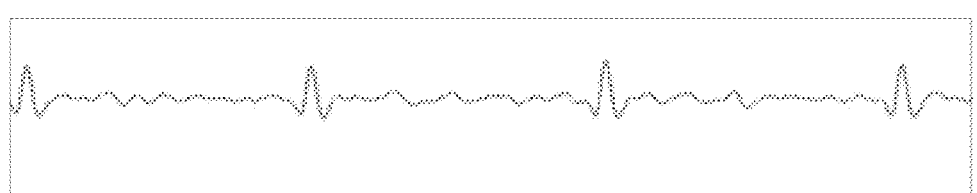
Figure 8F:
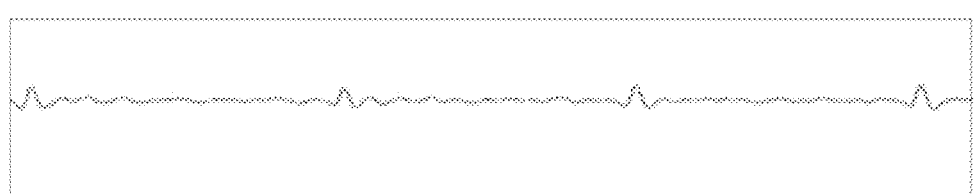
Figure 9A:
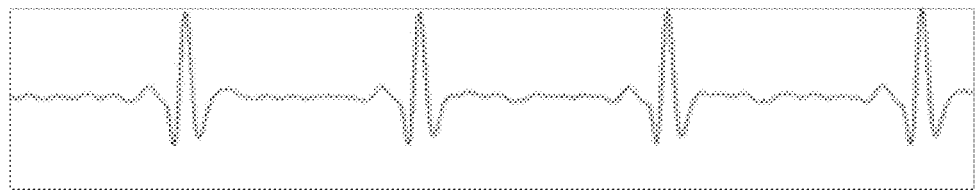
FIGS. 9a-9f respectively illustrate an oscillogram of physiological parameters of the heart of user B collected by use of different mattresses.
Figure 9B:
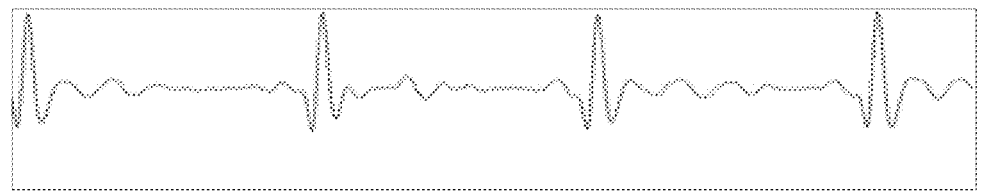
Figure 9C:
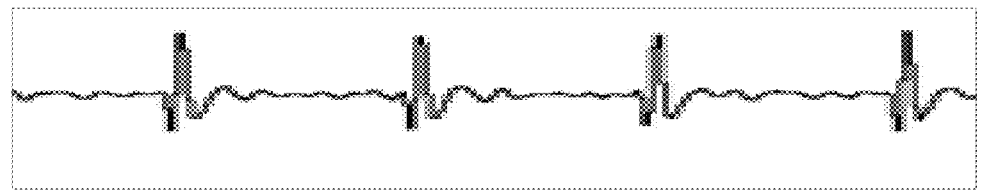
Figure 9D:
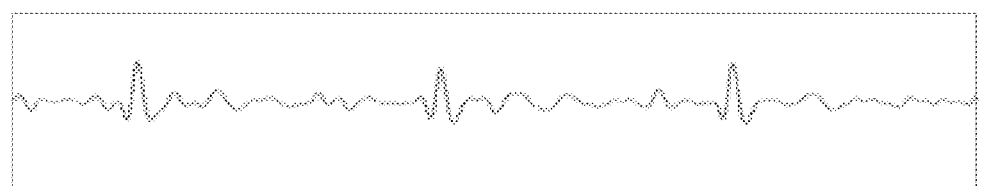
Figure 9E:
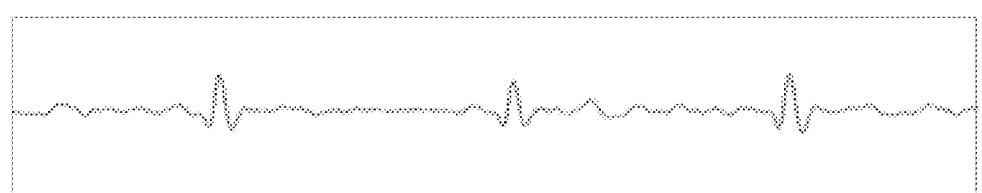
Figure 9F:
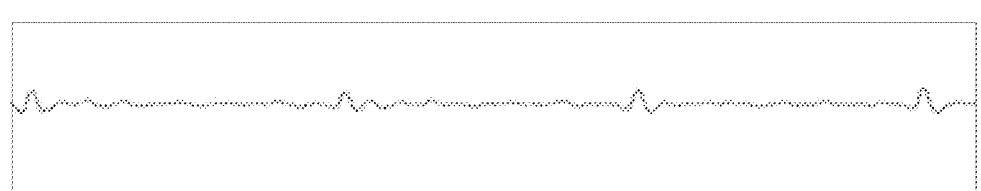

The experimental data suggest that numerical values of the width Wa of the first electrode and the width Wb of the second electrode have a significant influence on measurement of physiological parameters of the heart, which is hereby shown in FIGS. 8a-8f and FIGS. 9a-9f, wherein FIGS. 1, 2 and 7 are referred to for Wa and Wb. FIGS. 8a-8f respectively illustrate an oscillogram of physiological parameters of the heart of user A collected by use of different mattresses; and FIGS. 9a-9f respectively illustrate an oscillogram of physiological parameters of the heart of user B collected by use of different mattresses. The horizontal axis of the oscillogram denotes time, and the vertical axis of oscillogram denotes voltage representing the value of physiological parameters of the heart. The differences between the mattresses lies in the different width of the electrodes of the mattress. The oscillograms shown in FIGS. 8a and 9a are collected by a mattress where the width Wa of the first electrode and the width Wb of the second electrode are both 18 cm, wherein the peak value is about 2.8 V. The oscillograms shown in FIGS. 8b and 9b are collected by a mattress where the width Wa of the first electrode and the width Wb of the second electrode are both 15 cm, wherein the peak value is about 2.6 V. The oscillograms shown in FIGS. 8c and 9c are collected by a mattress where the width Wa of the first electrode and the width Wb of the second electrode are both 12 cm, wherein the peak value is about 2.0 V. The oscillograms shown in FIGS. 8d and 9d are collected by a mattress where the width Wa of the first electrode and the width Wb of the second electrode are both 9 cm, wherein the peak value is about 1.7 V. The oscillograms shown in FIGS. 8e and 9e are collected by a mattress where the width Wa of the first electrode and the width Wb of the second electrode are both 7 cm, wherein the peak value is about 1.0 V. The oscillograms shown in FIGS. 8f and 9f are collected by a mattress where the width Wa of the first electrode and the width Wb of the second electrode are both 4.5 cm, wherein the peak value is about 0.5 V.

On one hand, the first electrode and the second electrode, when in use, need to be located at two ends of the heart of the user, while the distance between the upper end of the heart and the shoulder is limited. Therefore, the width of the electrode is restricted by this distance. On the other hand, within a certain range, the larger the width of the electrode, the larger the contact area between the electrode and the human body, and thus the clearer the waveform, with no clutter. For example, if the width of the electrode is less than 7 cm, the peak value collected by the mattress may be lower than 1.0 V, which impacts the effectiveness in measurement of physiological parameters of the heart. In still another aspect, the larger the width of the electrode, the more material is required to produce the electrode, which increases the manufacturing cost of the mattress. By weighing the measurement result and cost, the width Wa of the first electrode and the width Wb of the second electrode may be selected from 7 cm to 18 cm. Optionally, the width Wa of the first electrode and the width Wb of the second electrode are the same.

As can be noticed from above data and design parameters, a mattress having an electrode width of 9 cm collects a peak value of about 1.7 V, which is sufficient for measuring physiological parameters of the heart. In addition, when the width of the electrode increases to 12 cm, the peak value does not observably grow. On this basis, preferably, the width Wa of the first electrode and the width Wb of the second electrode are from 9 cm to 12 cm.

Optionally, the space between the first electrode and second electrode may be from 11 cm to 25 cm, as shown by Wi in FIGS. 1, 2 and 7. Preferably, the space Wi is from 13 cm to 20 cm.

Figure 10A:
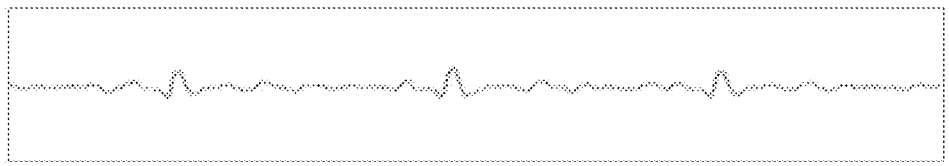
FIGS. 10a-10g respectively illustrate an oscillogram of physiological parameters of the heart of user A collected by use of different mattresses.
Figure 10B:
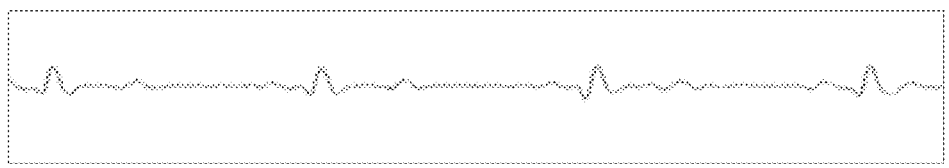
Figure 10C:
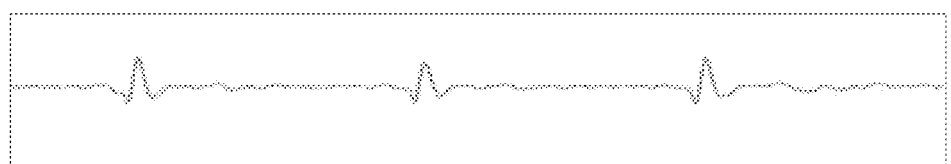
Figure 10D:
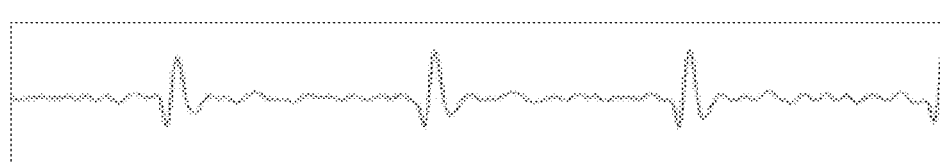
Figure 10E:
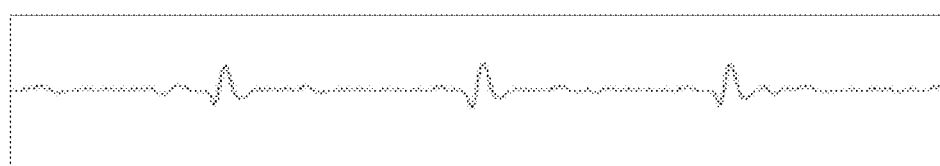
Figure 10F:
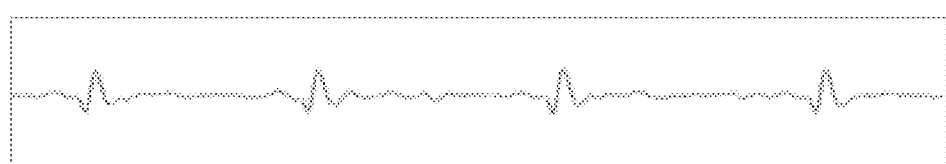
Figure 10G:
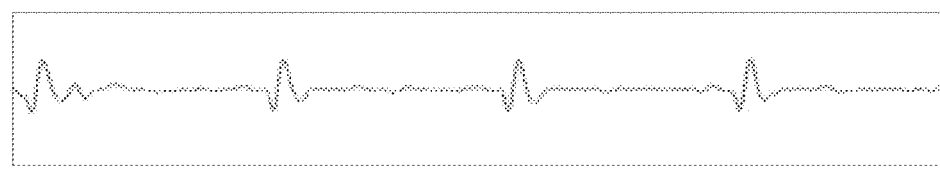
Figure 11A:
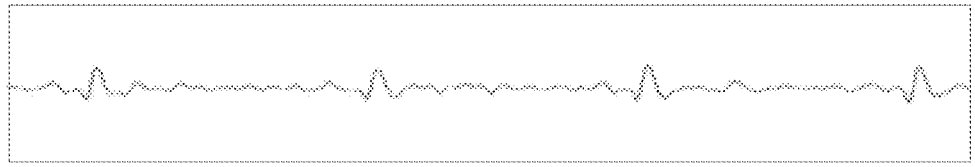
FIGS. 11a-11g respectively illustrate an oscillogram of physiological parameters of the heart of user B collected by use of different mattresses.
Figure 11B:
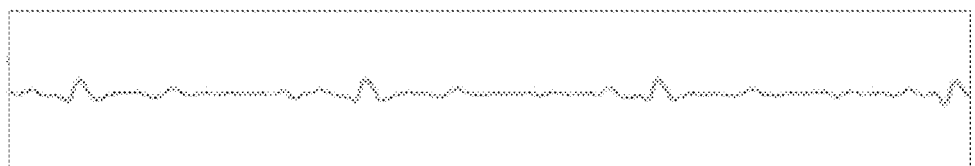
Figure 11C:
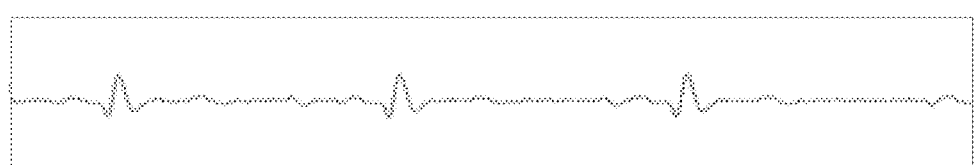
Figure 11D:
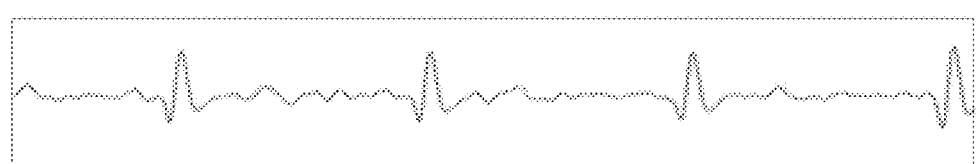
Figure 11E:
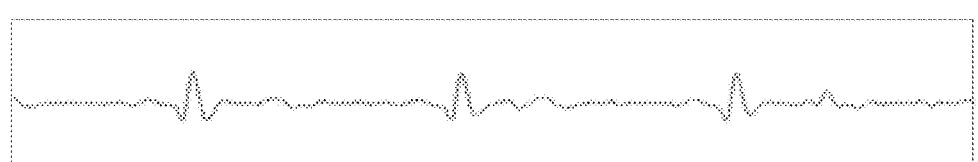
Figure 11F:
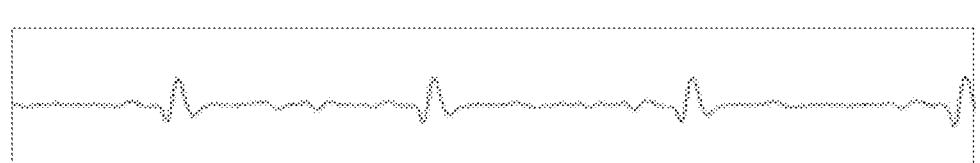
Figure 11G:
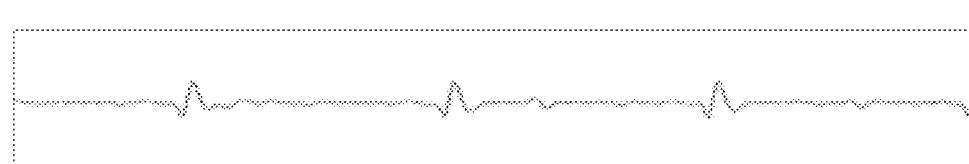

FIGS. 10a-10g respectively illustrate oscillogram of physiological parameters of the heart of user A collected by use of different mattresses; and FIGS. 11a-11g illustrate oscillogram of physiological parameters of the heart of user B collected by use of different mattresses. The horizontal axis of the oscillogram denotes time, and the vertical axis of the oscillogram denotes voltage representing the value of physiological parameters of the heart. The difference between the mattresses lies in the different space Wi between the electrodes of the mattresses. The oscillograms in FIG. 10a and FIG. 11a are collected by using a mattress with a space Wi of 30 cm between the electrodes, wherein the peak value is about 0.9 V. The oscillograms in FIG. 10b and FIG. 11b are collected by using a mattress with a space Wi of 29 cm between the electrodes, wherein the peak value is about 1.0 V. The oscillograms in FIG. 10c and FIG. 11c are collected by using a mattress with a space Wi of 20 cm between the electrodes, wherein the peak value is about 1.3 V. The oscillograms in FIG. 10d and FIG. 11d are collected by using a mattress with a space Wi of 15 cm between the electrodes, wherein the peak value is about 2.0 V. The oscillograms in FIG. 10e and FIG. 11e are collected by using a mattress with a space Wi of 13 cm between the electrodes, wherein the peak value is about 1.2 V. The oscillograms in FIG. 10f and FIG. 11f are collected by using a mattress with a space Wi of 11 cm between the electrodes, wherein the peak value is about 1.0 V. The oscillograms in FIG. 10g and FIG. 11g are collected by using a mattress with a space Wi of 9 cm between the electrodes, wherein the peak value is about 0.9 V.

As is shown by the experimental data, the numerical value of the space Wi holds obvious influence upon the collected measurement of physiological parameters of the heart. Best-quality signals are acquired when the first electrode and the second electrode collecting physiological parameters of the heart are located at the upper and lower ends of the heart respectively. Too wide or too narrow a space Wi may result in signals with too much clutter or too small amplitude. The space Wi between the electrodes of the mattress is preferably 15 cm, with the collected oscillogram shown in FIGS. 10d and 11d, wherein the waveform has a distinct peak and a large signal to noise ratio.

Optionally, the lengths of the first and second electrodes may be from 60 cm to 85 cm. Electrodes with such length may ensure a proper contact area with the human body even when the human body turns over on the mattress, thus guaranteeing the accuracy of measurement of the physiological parameters of the heart.

According to the embodiment of the present invention, the electromagnetic shield, the first electrode and the second electrode may comprise conductive fabric, such as conductive cloth. Conductive fabric is a conductor, which not only fulfills the function of electromagnetic shielding, but may also be used to measure potential difference signals. In addition, conductive fabric is relatively thin and flexible, and therefore, can make the mattress more comfortable. Optionally, material of the conductive fabric includes copper-nickel alloy. Copper and nickel are infinitely solid-soluble with each other to form copper-nickel alloy. Copper-nickel alloy has good malleability and is suitable for use as the metal conductor in conductive fabric.

Optionally, the thickness of the conductive fabric may be 1 mm to 1.8 mm. This thickness not only ensures that the conductive fabric contains an appropriate amount of metal conductor guaranteeing the accuracy of measurement, but also takes into consideration the comfort and cost of the mattress.

According to one embodiment of the present invention, the mattress body also comprises a protective layer. Preferably, the protective layer is a waterproof cloth or sheet. The mattress of the present application may be used for patients with various diseases, such as old people who are paralyzed in bed after a strike and cannot take care of themselves. On the one hand, the protective layer may effectively prevent the mattress from being comprised or inappropriate use, while maintaining the integrity of the mattress to extend its service life. Also, the protective layer effectively isolates the electrodes and the electromagnetic shield. If materials like urine or feces permeate downward from the electrodes and contact the electromagnetic shield, the conductivity of the comprising liquid would establish electrical connection between the electromagnetic shield and the electrodes, causing failure of the electromagnetic shield in carrying out electromagnetic shielding for the electrodes. The existence of the protective layer avoids the above problem.

According to one embodiment of the present invention, the mattress body may comprise synthetic fabric or cotton cloth. Wherein, the cotton cloth, especially double-layer cotton cloth, may help the electromagnetic shield with the electromagnetic shielding.

Figure 12:
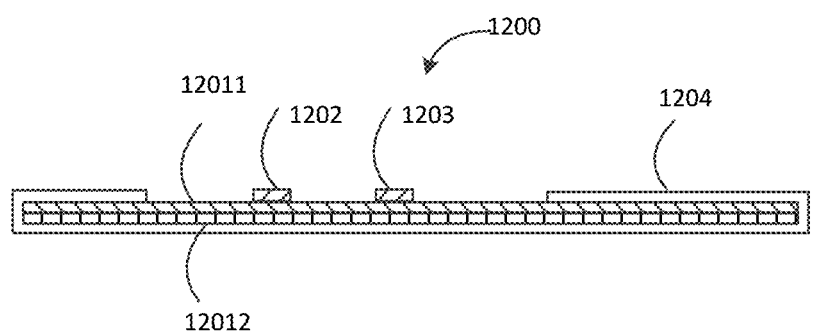
FIG. 12 is a sectional view of a mattress for measuring physiological parameters of a heart according to still another embodiment of the present invention.

FIG. 12 is a sectional view of a mattress 1200 according to another embodiment of the present invention. As shown in FIG. 12, the mattress 1200 comprises a protective layer 12011, cotton cloth 12012, a first electrode 1202, a second electrode 1203 and an electromagnetic shield 1204, wherein the protective layer 12011 constitutes a mattress body along with the cotton cloth 12012.

Figure 13A:
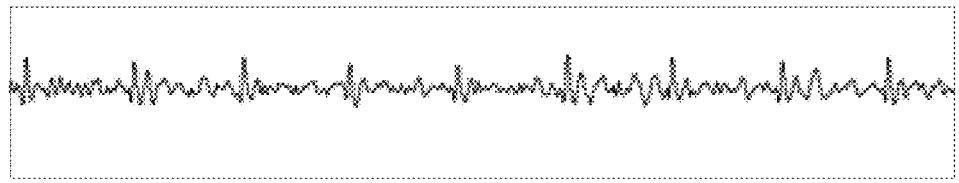
FIGS. 13a, 13b and 13c respectively, illustrate an oscillogram of physiological parameters of user A collected by use of different mattresses, and FIGS. 13d, 13e and 13f, respectively, illustrate an oscillogram of physiological parameters of user B collected by use of different mattresses.
Figure 13B:
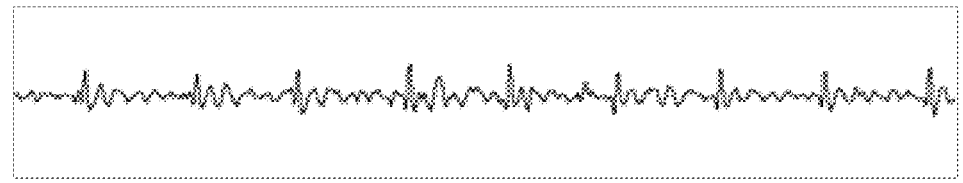
Figure 13C:
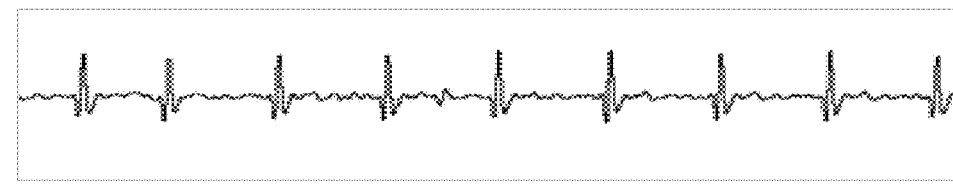
Figure 13D:
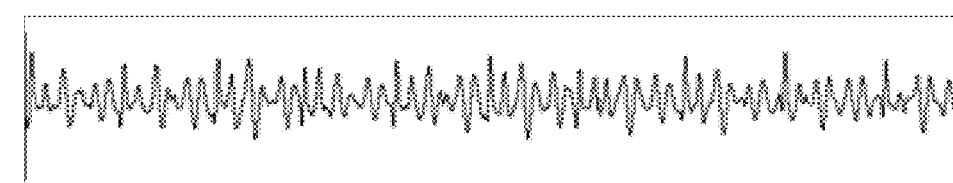
Figure 13E:
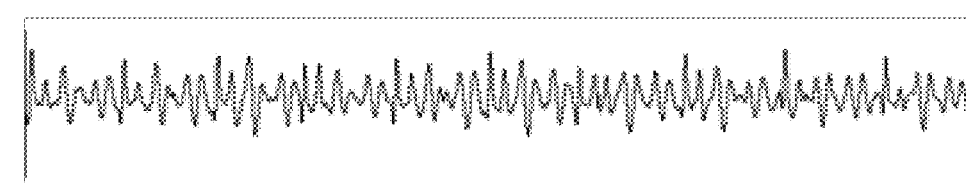
Figure 13F:
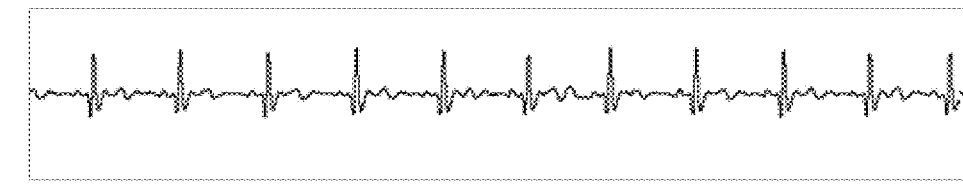

FIGS. 13a, 13b and 13c respectively illustrate an oscillogram of physiological parameters of user A collected by use of different mattresses, and FIGS. 13d, 13e and 13f respectively illustrate an oscillogram of physiological parameters of user B collected by use of different mattresses. The horizontal axis of the oscillogram denotes time, and the vertical axis of the oscillogram denotes voltage representing the value of physiological parameters of the heart. In the mattress used for collecting the oscillograms in FIGS. 13a and 13d, the mattress body is constituted by the protective layer alone; in the mattress used for collecting the oscillograms in FIGS. 13b and 13e, the mattress body is constituted by the protective layer and the synthetic fabric; in the mattress used for collecting the oscillograms in FIGS. 13c and 13f, the mattress body is constituted by the protective layer and the cotton cloth. The synthetic fabric per se is inclined to generate static electricity, and therefore, may cause signal interference with the electrodes, as shown in FIGS. 13b and 13e, which prevents the signal waveform from accurately reflecting the actual physiological parameters. As shown in FIGS. 13c and 13f, the cotton cloth successfully helps the electromagnetic shield with the electromagnetic shielding. As compared to FIGS. 13a, 13b, 13d and 13e respectively and correspondingly, the waveforms shown in FIGS. 13c and 13f more optimally reflect the actual physiological parameters of the user.

Figure 14:
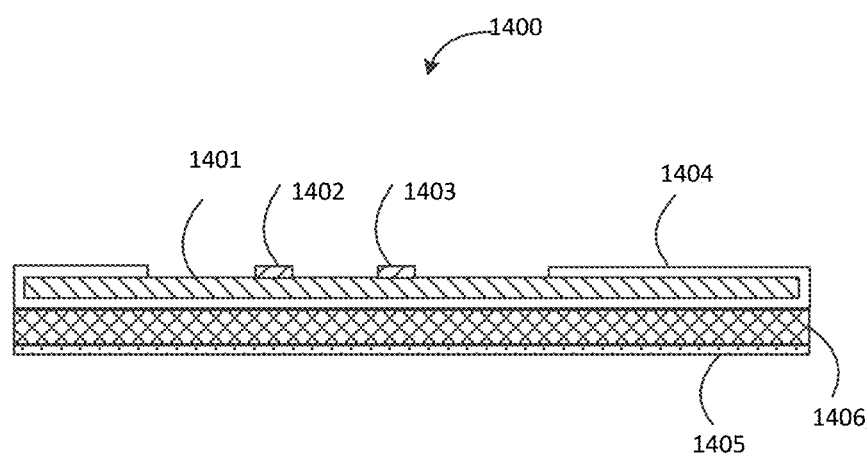
FIG. 14 is a sectional view of a mattress for measuring physiological parameters of a heart according to yet another embodiment of the present invention.

According to one embodiment of the present invention, the mattress also comprises a fixing layer, which is located on the lower surface of the mattress and has a rough surface. The fixing layer helps locate the mattress on the bed, preventing it from free movement. Thus, when the user lies down, it is guaranteed that the position of the electrodes relative to the user remain unchanged, so as to obtain accurate measurement results. Optionally, the mattress also comprises a sponge layer. The sponge layer may be located under the electromagnetic shield. The sponge layer can effectively improve the comfort of the mattress. FIG. 14 is a sectional view of a mattress 1400 according to another embodiment of the present invention. As shown in FIG. 14, the mattress 1400 is similar to the mattress 400, but the mattress 1400 comprises a mattress body 1401, a first electrode 1402, a second electrode 1403, an electromagnetic shield 1404, a fixing layer 1405 and a sponge layer 1406. The mattress 1400 does not move due to movements, such as turning over, of the user, and is very comfortable.

Figure 15:
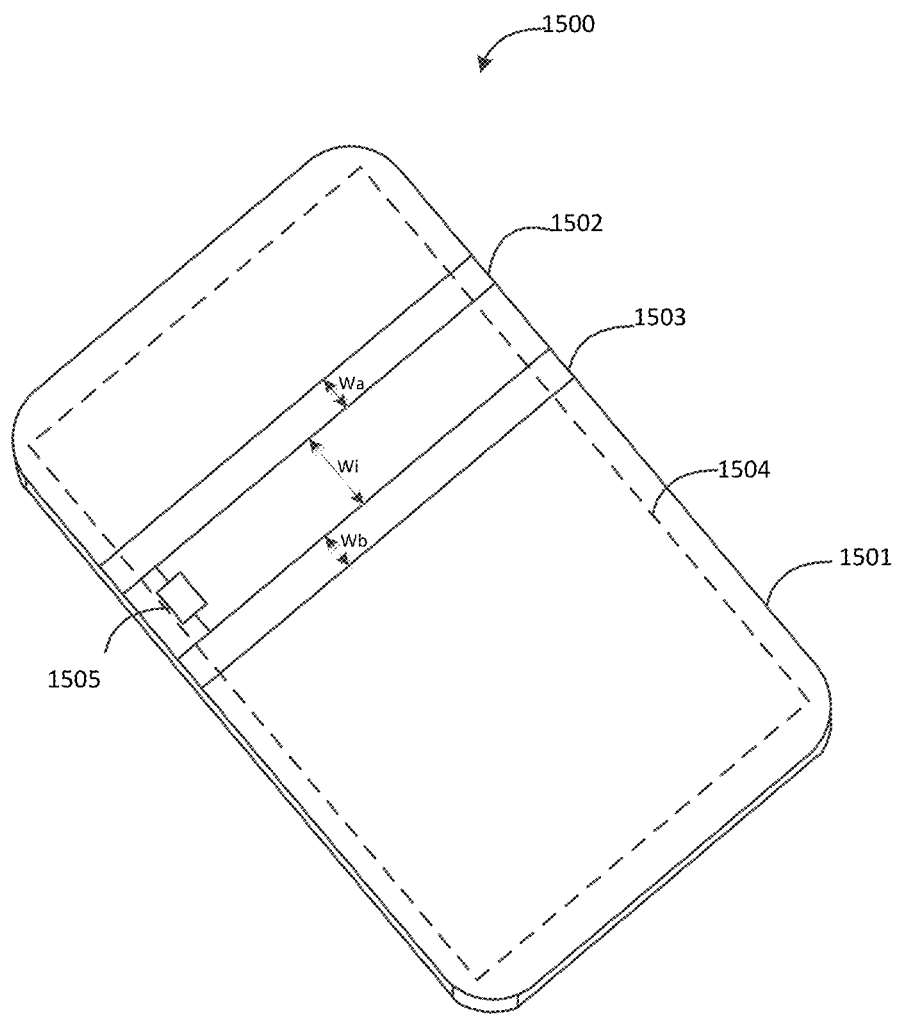
FIG. 15 is a schematic diagram of a mattress for measuring physiological parameters of a heart according to another embodiment of the present invention.

The mattress may also comprise a signal processor. FIG. 15 illustrates a mattress 1500 according to still another embodiment of the present invention. The mattress 1500 comprises a mattress body 1501, a first electrode 1502, a second electrode 1503, and an electromagnetic shield 1504 that are similar to the mattress body 101, the first electrode 102, the second electrode 103 and the electromagnetic shield 104 of the mattress 100, respectively. In comparison with the mattress 100, the mattress 1500 further comprises a signal processor 1505. As shown in FIG. 15, the signal processor 1505 is connected to the first electrode 1502 and the second electrode 1503, and is used for processing electrocardiosignals from the first electrode 1502 and the second electrode 1503 and generating physiological parameters of the heart according to the electrocardiosignals.

As discussed above, in the embodiment of the present invention, the first electrode 1502 and the second electrode 1503 are used to collect electrocardiosignals of the human body, so as to measure physiological parameters of the heart of the human body. Because of their low signal intensity, electrocardiosignals are susceptible to interferences. Therefore, the signal processor 1505 may be used to further process electrocardiosignals. For example, first of all, electrocardiosignals from the first electrode 1502 and the second electrode 1503 are amplified. Then, the amplified signals are filtered, so as to remove interfering noises and generate effective physiological parameters of the heart.

Those skilled in the art would understand that the term "connection" in the present invention may refer to physical connection or logical connection, such as wired connection and wireless connection. For example, the first electrode 1502 and the second electrode 1503 may transmit electrocardiosignals to the signal processor 1505 by means of Bluetooth, radio frequency, etc.

The signal processor may be embedded in the mattress body. For example, it may be embedded into the mattress body near the side of the mattress body. The signal processor will not affect the comfort by being embedded in the mattress body when the user is lying thereon, thus ensuring high user experiences.

According to one embodiment of the present invention, the mattress may also comprise a speaker, wherein a signal processor is also used for driving the speaker to give an alarm based on physiological parameters of the heart. When the state of the physiological parameters of the heart are lower than the first threshold or higher than the second threshold and last for a fixed period of time, such as 30 seconds, the signal processor may drive the speaker to give a buzzing sound, so as to warn the user and others that the user's heart may be in an abnormal state. Existence of the speaker enables the diseased user to get treatment in time, avoiding tragedy.

The present invention has been explained through the above embodiments, but it should be appreciated that the above embodiments are only for exemplary and illustrative purposes, rather than intended to limit the present invention within the scope of the embodiments as described. In addition, those skilled in the art would appreciate that the present invention is not limited to the above embodiments, and according to the teachings in the present invention, more variations and modifications may be made. These variations and modifications all fall within the scope of protection sought by the present invention. The protection scope of the present invention shall be defined by the appended claims and equivalent scope thereof.

What is claimed is:

1. A mattress for measuring physiological parameters of a heart, comprising
    a mattress body, a first electrode, a second electrode and an electromagnetic shield, wherein the first electrode and the second electrode are located on an upper surface of the mattress body, and the first electrode and the second electrode have a space therebetween, the first electrode is configured to be placed on an upper position of the heart and the second electrode is configured to be placed on a lower position of the heart, wherein
    the first and second electrodes have a width between 9-12 cm and a length from 60-85 cm and a distance between the first and second electrodes is between 13-20 cm;
    the electromagnetic shield, the first electrode and the second electrode comprise a conductive fabric, having a thickness of 1-1.8 mm;
    at least a portion of the electromagnetic shield is located on a lower surface of the mattress body and is insulated from the first electrode and the second electrode.

2. The mattress according to claim 1, wherein the electromagnetic shield has a width equal to that of the mattress body.

3. The mattress according to claim 2, wherein a portion of the electromagnetic shield located on the lower surface of the mattress body covers the entire lower surface of the mattress body.

4. The mattress according to claim 1, wherein the electromagnetic shield extends from the lower surface of the mattress body along a tail of the mattress body to the upper surface of the mattress body in the width of the electromagnetic shield.

5. The mattress according to claim 4, wherein, on the upper surface of the mattress body, a distance between the electromagnetic shield and the second electrode is from 20 cm to 40 cm.

6. The mattress according to claim 1, wherein the electromagnetic shield extends from the lower surface of the mattress body along a head of the mattress body to the upper surface of the mattress body in the width of the electromagnetic shield.

7. The mattress according to claim 6, wherein, on the upper surface of the mattress body, a distance between the electromagnetic shield and the first electrode is from 12 cm to 25 cm.

8. The mattress according to claim 1, wherein the electromagnetic shield extends from the lower surface of the mattress body along a head and a tail of the mattress body to the upper surface of the mattress body in the width of the electromagnetic shield.

9. The mattress according to claim 8, wherein, on the upper surface of the mattress body, a distance d1 between the electromagnetic shield and the first electrode and a distance d2 between the electromagnetic shield and the second electrode meet the following condition:

$$d_2 = a * d_1, a \in [1,2].$$

10. The mattress according to claim 8, wherein the electromagnetic shield has an end edge on the upper surface of the mattress body that is parallel to the head of the mattress.

11. The mattress according to claim 8, wherein the electromagnetic shield has a width equal to that of the mattress body, and a portion of the electromagnetic shield located on the upper surface of the mattress body is completely connected with the portion of the electromagnetic shield located on the lower surface of the mattress body on two side edges.

12. The mattress according to claim 1, wherein the electromagnetic shield extends from the lower surface of the mattress body along a side of the mattress body to the upper surface of the mattress body in the length of the electromagnetic shield.

13. The mattress according to claim 1, wherein the electromagnetic shield is electrically connected to a ground wire.

14. The mattress according to claim 1, wherein the electromagnetic shield comprises a first layer of electric conductor and a second layer of electric conductor that are insulated from each other; wherein the first layer of electric conductor has a lower electrical resistivity as well as a lower magnetoconductivity than the second layer of electric conductor.

15. The mattress according to claim 1, wherein the first electrode and the second electrode are rectangular and parallel to each other, and the first electrode and the second electrode are parallel to the head of the mattress.

16. The mattress according to claim 1, further comprises a signal processor, which is connected to the first electrode and the second electrode, for processing electrocardiosignals from the first electrode and the second electrode and generating physiological parameters of the heart according to the electrocardiosignals.

* * * * *